United States Patent
Oevering et al.

(10) Patent No.: US 7,537,745 B2
(45) Date of Patent: May 26, 2009

(54) PROCESS FOR PRODUCING CYCLOHEXANONE OXIME BY MIXING AN ACIDIC AQUEOUS SOLUTION COMPRISING HYDROXYLAMMONIUM AND PHOSPHATE WITH NITRIC ACID

(75) Inventors: Hendrik Oevering, Elsloo (NL); Arno H Benneker, Doenrade (NL)

(73) Assignee: DSM IP Assets B.V., Heerlen (NL)

( * ) Notice: Subject to any disclaimer, the term of this patent is extended or adjusted under 35 U.S.C. 154(b) by 651 days.

(21) Appl. No.: 10/538,045

(22) PCT Filed: Dec. 10, 2003

(86) PCT No.: PCT/NL03/00877

§ 371 (c)(1),
(2), (4) Date: Jun. 29, 2005

(87) PCT Pub. No.: WO2004/052780

PCT Pub. Date: Jun. 24, 2004

(65) Prior Publication Data

US 2006/0115404 A1    Jun. 1, 2006

(30) Foreign Application Priority Data

Dec. 11, 2002  (EP) .................................. 02080204

(51) Int. Cl.
*C01B 21/06*  (2006.01)
(52) U.S. Cl. ...................................... 423/302; 564/267
(58) Field of Classification Search ................. 423/302
See application file for complete search history.

(56) References Cited

U.S. PATENT DOCUMENTS

| 3,997,607 A | * | 12/1976 | de Rooij | 564/259 |
| 2006/0115404 A1 | * | 6/2006 | Oevering et al. | 423/302 |

FOREIGN PATENT DOCUMENTS

| GB | 1 326 405 |   | 8/1973 |   |
| WO | WO 01/94296 | * | 12/2001 | 249/8 |
| WO | WO 01/94296 A1 |   | 12/2001 |   |
| WO | WO 01/94298 A1 |   | 12/2001 |   |

OTHER PUBLICATIONS

International Search Report.

* cited by examiner

*Primary Examiner*—Melvin C Mayes
*Assistant Examiner*—Kenneth Vaden
(74) *Attorney, Agent, or Firm*—Nixon & Vanderhye P.C.

(57) ABSTRACT

The invention relates to a process for mixing a first acidic aqueous solution comprising hydroxylammonium and phosphate with a second acidic aqueous solution comprising nitric acid at a temperature between 20 and 80° C. resulting in a third acidic aqueous solution comprising hydroxylammonium, phosphate and nitric acid, wherein in the third acidic aqueous solution the total acid concentration minus the phosphate concentration is lower than 0.523*ln([hydroxylammonium]/1.25)+422/(T+81) whereby [hydroxylammonium] is the concentration of hydroxylammonium in the third acidic aqueous solution, T is the temperature of the third acidic aqueous solution expressed in ° C. and all concentrations are expressed in mol/l.

18 Claims, 1 Drawing Sheet

US 7,537,745 B2

PROCESS FOR PRODUCING CYCLOHEXANONE OXIME BY MIXING AN ACIDIC AQUEOUS SOLUTION COMPRISING HYDROXYLAMMONIUM AND PHOSPHATE WITH NITRIC ACID

This application is the US national phase of international application PCT/NL2003/000877 filed 10 Dec. 2003 which designated the U.S. and claims benefit of EP 02080204.7, dated 11 Dec. 2002, the entire content of which is hereby incorporated by reference.

The invention relates to a process for mixing a first acidic aqueous solution comprising hydroxylammonium and phosphate with a second acidic aqueous solution comprising nitric acid, resulting in a third acidic aqueous solution comprising hydroxylammonium, phosphate and nitric acid.

Cyclohexanone oxime can be prepared in a process in which an aqueous reaction medium is cycled from a hydroxylammonium synthesis reactor in which hydroxylammonium is prepared by catalytic reduction of nitrate with hydrogen to a cyclohexanone oxime synthesis reactor in which cyclohexanone oxime is produced by reaction of hydroxylammonium with cyclohexanone and from the cyclohexanone oxime synthesis reactor back to the hydroxylammonium synthesis reactor. To make up for the nitrate that is reduced in the hydroxylammonium synthesis reactor, nitric acid can be introduced into the aqueous reaction medium by mixing a nitric acid solution with the aqueous solution leaving the cyclohexanone oxime synthesis zone. The aqueous reaction medium leaving the cyclohexanone oxime synthesis reactor may comprise unreacted hydroxylammonium. Said unreacted hydroxylammonium may decompose as a result of the mixing with the nitric acid solution, this decomposition being disadvantageous, as hydroxylammonium is a useful product.

CN-A-1281849 discloses the use of a static mixer for mixing both solutions. However, in the mixed solution decomposition of hydroxylammonium may still occur.

The object of the present invention is to provide a process for mixing a first acidic aqueous solution comprising hydroxylammonium and phosphate with a second acidic aqueous solution comprising nitric acid, resulting in a third acidic aqueous solution comprising hydroxylammonium, phosphate and nitric acid, in which decomposition of hydroxylammonium in the third acidic aqueous solution is prevented or at least reduced.

This object is achieved in that in the third acidic aqueous solution the total acid concentration minus the phosphate concentration is lower than $0.523*\ln([\text{hydroxylammonium}]/1.25)+422/(T+81)$ whereby [hydroxylammonium] is the concentration of hydroxylammonium in the third acidic aqueous solution, T is the temperature of the third acidic aqueous solution expressed in °C. and all concentrations are expressed in mol/l.

It has in particular been found that decomposition of hydroxylammonium can be reduced or even prevented by having a hydroxylammonium concentration in the first and/or third acidic aqueous solution sufficiently high such that the total acid concentration minus the phosphate concentration in the third acidic aqueous solution is lower than $0.523*\ln([\text{hydroxylammonium}]/1.25)+422/(T+81)$. Obtaining a sufficiently high hydroxylammonium concentration in the first acidic aqueous solution can for example be achieved by adding hydroxylammonium to an acidic aqueous solution comprising hydroxylammonium to obtain the first acidic aqueous solution. Obtaining a sufficiently high hydroxylammonium concentration in the third acidic aqueous solution can for example be achieved by adding hydroxylammonium to the third acidic aqueous solution and/or by performing the mixing of the first and second acidic aqueous solution in a hydroxylammonium reactor in which hydroxylammonium is prepared by catalytic reduction of nitrate with hydrogen.

As used herein, the total acid concentration of an acidic aqueous solution, for instance the first, second, third and fourth acidic aqueous solution, is preferably measured by titration to a pH of 4.2. Preferably, said titration is performed by adding 5 ml of the acidic aqueous solution to 50 ml distilled water and titration with a 0.25 N NaOH solution to a pH of 4.2. In an acidic aqueous solution comprising $H_3PO_4$ and $HNO_3$ as the acids, the total acid concentration is a measure for the sum of the concentration of $H_3PO_4$ and the concentration of $HNO_3$. Preferably the total acid concentration in the first acidic aqueous solution is higher than 0.1 mol/l and lower than 6 mol/l.

The process according to the invention comprises mixing a first acidic aqueous solution with a second acidic aqueous solution. The mixture obtained as a result of said mixing is, as used herein, also referred to as third acidic aqueous solution.

Preferably, the process comprises mixing the first acidic aqueous solution with the second acidic aqueous solution at a temperature between 20 and 80° C.

The first acidic aqueous solution comprises hydroxylammonium and phosphate. The second acidic aqueous solution comprises nitric acid. Any suitable first acidic aqueous solution and a second acidic aqueous solution may be used, such that the mixing thereof results in a third acidic aqueous solution in which $$c_{acid}(3)-c_{phosphate}(3)<0.523*\ln(c_{hyam}(3)/1.25)+422/(T(3)+81)$$

wherein $c_{acid}(3)$=total acid concentration in the third acidic aqueous solution, expressed in mol/l, $C_{phosphate}(3)$=phosphate concentration in the third acidic aqueous solution, expressed in mol/l, $c_{hyam}(3)$=concentration hydroxylammonium in the third acidic aqueous solution, expressed in mol/l, T(3)=temperature of the third acidic aqueous solution expressed in °C. Based on the present disclosure, the skilled man can apply any suitable combination of conditions such as for instances quantities of first acidic aqueous solution and second acidic aqueous solution to be mixed, a suitable acidity and suitable concentration of hydroxylammonium in the first acidic aqueous solution, a suitable acidity of the second aqueous solution, a suitable concentration of hydroxylammonium in the third acidic aqueous solution and a suitable temperature.

In a preferred embodiment, the invention provides a process comprising mixing a first acidic aqueous solution comprising hydroxylammonium and phosphate with a second acidic aqueous solution comprising nitric acid, preferably at a temperature between 20 and 80° C., resulting in a third acidic aqueous solution comprising hydroxylammonium, phosphate and nitric acid, wherein $$(c_{acid}(1)*V_1+c_{acid}(2)*V_2)/(V_1+V_2)-(c_{phosphate}(1)*V_1+c_{phosphate}(2)*V_2)/(V_1+V_2)<0.523*\ln((c_{hyam}(1)*V_1+c_{hyam}(2)*V_2)/(V_1+V_2)/1.25)+422/(T(3)+81)$$

wherein $c_{acid}(1)$ and $c_{acid}(2)$ are the total acid concentration in the first acidic aqueous solution and in the second acidic aqueous solution respectively, expressed in mol/l.

$c_{phosphate}(1)$ and $c_{phosphate}(2)$ are the phosphate concentration in the first acidic aqueous solution and in the second acidic aqueous solution respectively, expressed in mol/l.

$c_{hyam}(1)$ and $c_{haym}(2)$ are concentration hydroxylammonium in the first acidic aqueous solution and in the second acidic aqueous solution respectively, expressed in mol/l.

T(3) temperature of the third acidic aqueous solution.

$V_1$ and $V_2$ are the volume of the first acidic aqueous solution and second acidic aqueous solution respectively. The skilled man will understand that in a continuous process $V_1$ and $V_2$ refer to the flow rates of the first and second acidic aqueous solution, expressed in volume of first acidic aqueous solution per second and volume of second acidic aqueous solution per second respectively. This embodiment is an advantageous way for obtaining the third acidic aqueous solution according to the invention and for the prevention of decomposition of hydroxylammonium.

In general the hydroxylammonium concentration in the first acidic aqueous solution is higher than 0.002 mol/l, for instance higher than 0.005 mol/l, for instance higher than 0.01 mol/l, for instance higher than 0.02 mol/l. Typically, the hydroxylammonium concentration in the first acidic aqueous solution is below 2 mol/l, preferably below 0.2 mol/l.

In an embodiment, the process according to the invention comprises preparing hydroxylammonium by catalytic reduction of nitrate with hydrogen in a hydroxylammonium synthesis reactor. The catalytic reduction of nitrate with hydrogen can be represented by the following equation:

$$2H_3PO_4 + NO_3^- + 3H_2 \rightarrow NH_3OH^+ + 2H_2PO_4^- + 2H_2O$$

In an embodiment, the process according to the invention comprises preparing cyclohexanone oxime by reaction of hydroxylammonium and cyclohexanone in a cyclohexanone oxime synthesis reactor. The reaction of hydroxylammonium and cyclohexanone can be represented by the following equation:

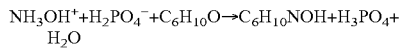

$$NH_3OH^+ + H_2PO_4^- + C_6H_{10}O \rightarrow C_6H_{10}NOH + H_3PO_4 + H_2O$$

In an embodiment the process according to the invention comprises cycling an aqueous reaction medium from the hydroxylammonium synthesis reactor to the cyclohexanone oxime synthesis reactor, and from the cyclohexanone oxime synthesis reactor back to the hydroxylammonium synthesis reactor In an embodiment of the process according to the invention, an aqueous reaction medium leaving the cyclohexanone oxime synthesis reactor is used a the first acidic aqueous solution. The use of the aqueous reaction medium leaving the cyclohexanone oxime synthesis reactor as first acidic aqueous solution may involve a process wherein the aqueous reaction medium leaving the cyclohexanone oxime synthesis reactor is, as the first acidic aqueous medium, mixed with the second acidic aqueous solution, resulting in the third acidic aqueous solution. In an embodiment, the aqueous solution leaving the cyclohexanone oxime reactor may be subjected to extraction prior to mixing the aqueous reaction mixture with the second acidic aqueous solution. In an embodiment, part of the water may be separated from the aqueous reaction mixture leaving the cyclohexanone oxime synthesis reactor by stripping prior to mixing the aqueous reaction mixture with the second acidic aqueous solution. In an embodiment, the aqueous reaction mixture leaving the cyclohexanone oxime synthesis reactor may, optionally after extraction and/or separation of water from the aqueous reaction mixture, be separated into at least a first part and a second part, and the first part of the aqueous reaction medium may be mixed with the second acidic aqueous solution. Nitrogen oxides may be absorbed and oxidized in said second part to prepare nitric acid and to obtain the second acidic aqueous solution.

In an embodiment of the process according to the invention, the process comprises adding hydroxylammonium to an acidic aqueous solution comprising hydroxylammonium to obtain the first acidic aqueous solution. After said adding, the resulting first acidic aqueous solution can be mixed with the second acidic aqueous solution. In another embodiment, the process according to the invention comprises adding hydroxylammonium to the third acidic aqueous solution during said mixing. Using the disclosure of the present invention, the skilled man can determine the amount of hydroxylammonium to be added to the acidic aqueous solution that is sufficient to prevent decomposition of hydroxylammonium. It is surprising that adding extra hydroxylammonium to a solution comprising hydroxylammonium can assist in preventing decomposition of hydroxylammonium. In an embodiment of the process according to the invention, the acidic aqueous solution to which hydroxylammonium is added is an aqueous reaction medium leaving the cyclohexanone oxime synthesis reactor. In an embodiment, the invention provides a process comprising cycling an aqueous reaction medium from the hydroxylammonium synthesis reactor to the cyclohexanone oxime synthesis reactor and from the cyclohexanone oxime synthesis reactor back to the hydroxylammonium synthesis reactor, the aqueous reaction medium leaving the cyclohexanone oxime synthesis reactor comprising hydroxylammonium; adding hydroxylammonium to the aqueous reaction medium leaving the cyclohexanone oxime synthesis reactor to obtain the first acidic aqueous solution; and mixing the first acidic aqueous solution with the second acidic aqueous solution. In a preferred embodiment, the aqueous reaction medium leaving the cyclohexanone oxime synthesis reactor is, optionally after having been subjected to extraction and/or separation of water from the aqueous reaction mixture by stripping, separated into at least a first part and a second part, and hydroxylammonium is advantageously added to the first part of the aqueous reaction medium; and nitrogen oxides are advantageously absorbed and/or oxidized in the second part of the aqueous reaction medium to prepare nitric acid to obtain the second acidic aqueous solution. This embodiment has the advantage that absorption and/or oxidation of nitrogen oxides may be effected without loss of added hydroxylammonium.

In a preferred embodiment, an aqueous reaction medium leaving a hydroxylammonium synthesis reactor is used to add said hydroxylammonium to an acidic aqueous solution. In a preferred embodiment, the process comprises adding part of the aqueous reaction medium leaving the hydroxylammonium synthesis reactor to an acidic aqueous solution, preferably to the aqueous reaction medium leaving the cyclohexanone oxime synthesis reactor. In such embodiments any part of the aqueous reaction medium leaving the hydroxylammonium synthesis reactor may be used to add hydroxylammonium to said acidic aqueous reaction medium. Preferably, 1-50% by volume, more preferably, 5-30% by volume may be used.

Generally, the phosphate concentration in the first acidic aqueous solution is higher than 2.0 mol/l. Preferably, the phosphate concentration is such that no crystallization occurs, which depends amongst other things on the temperature and the concentration of other components in the aqueous solution. Generally, the phosphate concentration in the first acidic aqueous solution is lower than 8 mol/l, preferably lower than 5 mol/l. As used herein, the phosphate concentration is defined as the sum concentration of all phosphates, irrespective of the form in which they are present, expressed in mol per liter of aqueous solution. Phosphates may be present as $PO_4^{3-}$, $HPO_4^{2-}$, $H_2PO_4^-$, $H_3PO_4$, salts of $PO_4^{3-}$, $HPO_4^{2-}$, $H_2PO_4^-$, and/or combinations thereof. Preferably, the first acidic aqueous solution comprising hydroxylammonium and phosphate is a phosphate buffered solution. Generally, the first acidic aqueous solution comprises ammonium and/or nitrate.

Any suitable acidic aqueous solution comprising nitric acid can be used as the second acidic aqueous solution. The second acidic aqueous solution comprising nitric acid may be obtained by absorbing and oxidizing nitrogen oxides in an aqueous solution. It is also possible to use a concentrated nitric acid solution as the second acidic aqueous solution. Preferably such a concentrated nitric acid solution contains 30-75% by weight of nitric acid. In a preferred embodiment, an aqueous reaction medium leaving the cyclohexanone oxime synthesis reactor is, optionally after separation of water from the aqueous reaction mixture, separated into at least a first part and a second part, and nitrogen oxides are advantageously absorbed and/or oxidized in the second part of the aqueous reaction medium to obtain, optionally after mixing with a, preferably concentrated, nitric acid solution, the second acidic aqueous solution.

Nitrogen oxides may be obtained from an ammonia-oxidation. The oxidation of ammonia can be represented by the following equation:

$$4\ NH_3 + 5O_2 \rightarrow 4\ NO + 6H_2O$$

The absorption and oxidation of nitrogen oxides in an aqueous solution to prepare nitric acid can be represented by the following equations:

$$2\ NO + O_2 \rightarrow 2\ NO_2$$

$$4\ NO_2 + O_2 + 2\ H_2O \rightarrow 4HNO_3$$

$$3\ NO_2 + H_2O \rightarrow 2\ HNO_3 + NO$$

There is no specific upper limit for the nitric acid concentration in the second acidic aqueous solution.

Generally, the phosphate concentration in the third acidic aqueous solution is higher than 2.0 mol/l. Preferably, the phosphate concentration is such that no crystallization occurs, which depends amongst other things on the temperature and the concentration of other components in the third acidic aqueous solution. Generally, the phosphate concentration in the third acidic aqueous solution is lower than 8 mol/l, preferably lower than 5 mol/l. As used herein, the phosphate concentration is defined as the sum concentration of all phosphates, irrespective of the form in which they are present, expressed in mol per liter of aqueous solution. Phosphates may be present as $PO_4^{3-}$, $HPO_4^{2-}$, $H_2PO_4^-$, $H_3PO_4$, salts of $PO_4^{3-}$, $HPO_4^{2-}$, $H_2PO_4^-$, and/or combinations thereof. Preferably, the third acidic aqueous solution comprising hydroxylammonium and phosphate is a phosphate buffered solution. Generally, the third acidic aqueous solution comprises ammonium and/or nitrate. Surprisingly, it has been found that decomposition of hydroxylammonium in the third acidic aqueous solution may be reduced or even prevented by increasing the hydroxylammonium concentration in the third acidic aqueous solution, for instance by addition of hydroxylammonium or by enrichment of hydroxylammonium in a hydroxylammonium synthesis reactor There is no specific upper limit for the hydroxylammonium concentration in the third acidic aqueous solution. Preferably, the hydroxylammonium concentration in the third acidic aqueous solution is lower than 2.5 mol/l.

The temperature of the mixture obtained as a result of said mixing, as used herein also referred to as third acidic aqueous solutions is preferably between 20 and 80° C. Preferably, the temperature of the third acidic aqueous solution is between 25 and 60° C. The temperature may also be between 20 and 40° C., for instance in an embodiment wherein the mixing of the first acidic aqueous solution with the second acidic aqueous solution is effected prior to feeding the third or fourth acidic aqueous solution to the hydroxylammonium synthesis reactor.

Mixing of the first acidic aqueous solution with the second acidic aqueous solution may be performed in any suitable manner, for instance by continuous merging the two acidic aqueous solutions supplied in a continuous flow and/or by using a mixer, a flow or line mixer, an agitated vessel or a bubble column. The mixing may be performed with a turbine stirrer or a static mixer.

After mixing the first acidic aqueous solution with the second acidic aqueous solution resulting in the third acidic aqueous solution, the concentration of nitric acid in the third acidic aqueous solution may be further increased by mixing the third acidic aqueous solution with an acidic aqueous solution comprising nitric acid, preferably at a temperature between 20 and 80° C., resulting in a fourth acidic aqueous solution comprising hydroxylammonium, phosphate and nitric acid whereby the total acid concentration minus the phosphate concentration in the fourth acidic aqueous solution is lower than $0.523*\ln([\text{hydroxylammonium}]/1.25)+422/(T+81)$ wherein [hydroxylammonium] is the concentration of hydroxylammonium in the fourth acidic aqueous solution, T is the temperature of the fourth acidic aqueous solution expressed in ° C. and all concentrations are expressed in mol/l.

Preferably the total acid concentration in the fourth acidic aqueous solution is higher than 0.1 mol/l and lower than 6 mol/l.

Generally, the phosphate concentration in the fourth acidic aqueous solution is higher than 2.0 mol/l. Preferably, the phosphate concentration is such that no crystallization occurs, which depends amongst other things on the temperature and the concentration of other components in the aqueous solution. Generally, the phosphate concentration in the fourth acidic aqueous solution is lower than 8 mol/l, preferably lower than 5 mol/l. As used herein, the phosphate concentration is defined as the overall concentration of all phosphates, irrespective of the form in which they are present, expressed in mol per liter of aqueous solution. Phosphates may be present as $PO_4^{3-}$, $HPO_4^{2-}$, $H_2PO_4^-$, $H_3PO_4$, salts of $PO_4^{3-}$, $HPO_4^{2-}$, $H_2PO_4^-$, and/or combinations thereof. Preferably, the fourth acidic aqueous solution comprising hydroxylammonium and phosphate is a phosphate buffered solution. Generally, the fourth acidic aqueous solution comprises ammonium and/or nitrate.

The preferred upper limit for the total acid concentration minus the phosphate concentration in the fourth acidic aqueous solution is determined by the hydroxylammonium concentration ([hydroxylammonium]) and the temperature (T) in the fourth acidic aqueous solution. The total acid concentration minus the phosphate concentration is preferably such that it is lower than $0.523*\ln([\text{hydroxylammonium}]/1.25)+422/(T+81)$ whereby all concentrations are expressed in mol/l.

There is no specific upper limit for the hydroxylammonium concentration in the fourth acidic aqueous solution. Preferably, the hydroxylammonium concentration in the fourth acidic aqueous solution is lower than 2.5 mol/l.

The temperature of the fourth acidic aqueous solution is preferably between 20 and 80° C. Preferably, the temperature is between 25 and 60° C. The temperature may also be between 20 and 40° C., for instance in an embodiment wherein the mixing of the third acidic aqueous solution with the acidic aqueous solution comprising nitric acid is effected prior to feeding the fourth mixture to the hydroxylammonium synthesis reactor.

Mixing of the third acidic aqueous solution with an acidic aqueous solution comprising nitric acid may be performed by continuous merging the two acidic aqueous solutions supplied in a continuous flow and/or by using a mixer, a flow or line mixer, an agitated vessel or a bubble column. The mixing may be performed with a turbine stirrer or a static mixer.

In preferred embodiment, the process comprises adding hydroxylammonium to the third acidic aqueous solution prior to mixing the third acidic aqueous solution with the acidic aqueous solution comprising nitric acid to form the fourth acidic aqueous solution.

In a preferred embodiment, an aqueous reaction medium leaving a hydroxylammonium synthesis reactor is used to add said hydroxylammonium to the third acidic aqueous solution. In a preferred embodiment, the process comprises adding part of the aqueous reaction medium leaving the hydroxylammonium synthesis reactor to the third acidic aqueous solution. Preferably, 1-50% by volume, more preferably, 5-30% by volume may be used.

In an embodiment the mixing of the first and second acidic aqueous solution resulting in the third acidic aqueous solution is performed before the third acidic aqueous solution is fed to the hydroxylammonium synthesis reactor. In still another embodiment this third acidic aqueous solution is mixed with an acidic aqueous solution comprising nitric acid resulting in the fourth acidic aqueous solution before this fourth acidic aqueous solution is fed to the hydroxylammonium synthesis reactor.

In another embodiment the mixing of the first acidic aqueous solution with the second acidic aqueous solution comprising nitric acid is performed in the hydroxylammonium synthesis reactor. This embodiment preferably comprises feeding the first acidic aqueous solution and the second acidic aqueous solution separately to the hydroxylammonium synthesis reactor. In this embodiment, the resulting third acidic aqueous solution is present in the hydroxylammonium synthesis reactor. In this embodiment, the third acidic aqueous solution is preferably enriched in hydroxylammonium in the hydroxylammonium synthesis reactor. In an embodiment, the invention provides a process comprising feeding a first acidic aqueous solution to a hydroxylammonium synthesis reactor, said first acidic aqueous solution comprising hydroxylammonium and phosphate; feeding a second acidic aqueous solution to a hydroxylammonium synthesis reactor, said second acidic aqueous solution comprising nitric acid; preparing hydroxylammonium in said hydroxylammonium synthesis reactor by catalytic reduction of nitrate with hydrogen; wherein in the hydroxylammonium synthesis reactor the total acid concentration minus the phosphate concentration is lower than $0.523*\ln([\text{hydroxylammonium}]/1.25)+422/(T+81)$ whereby [hydroxylammonium] is the concentration of hydroxylammonium in the hydroxylammonium synthesis reactor, T is the temperature in the hydroxylammonium synthesis reactor expressed in °C. and all concentrations are expressed in mol/l.

In a preferred embodiment, the invention comprises mixing the third acidic aqueous solution and the acidic aqueous solution comprising nitric acid in the hydroxylammonium synthesis reactor. This embodiment preferably comprises feeding the third acidic aqueous solution and the acidic aqueous solution comprising nitric acid separately to the hydroxylammonium synthesis reactor. In this embodiment, the resulting fourth acidic aqueous solution is present in the hydroxylammonium synthesis reactor. In this embodiment, the fourth acidic aqueous solution is preferably enriched in hydroxylammonium in the hydroxylammonium synthesis reactor. In an embodiment, the invention provides a process comprising feeding the third acidic aqueous solution to a hydroxylammonium synthesis reactor, said third acidic aqueous solution comprising hydroxylammonium and phosphate; feeding an acidic aqueous solution to a hydroxylammonium synthesis reactor, said acidic aqueous solution comprising nitric acid; preparing hydroxylammonium in said hydroxylammonium synthesis reactor by catalytic reduction of nitrate with hydrogen; wherein in the hydroxylammonium synthesis reactor the total acid concentration minus the phosphate concentration is lower than $0.523*\ln([\text{hydroxylammonium}]/1.25)+422/(T+81)$ whereby [hydroxylammonium] is the concentration of hydroxylammonium in the hydroxylammonium synthesis reactor, T is the temperature in the hydroxylammonium synthesis reactor expressed in °C. and all concentrations are expressed in mol/l.

The mixing in the hydroxylammonium synthesis reactor preferably is performed by using a bubble column as a hydroxylammonium synthesis reactor.

Preferably, the process according to the invention is a continuous process.

DESCRIPTION OF AN EMBODIMENT

Figure 1:
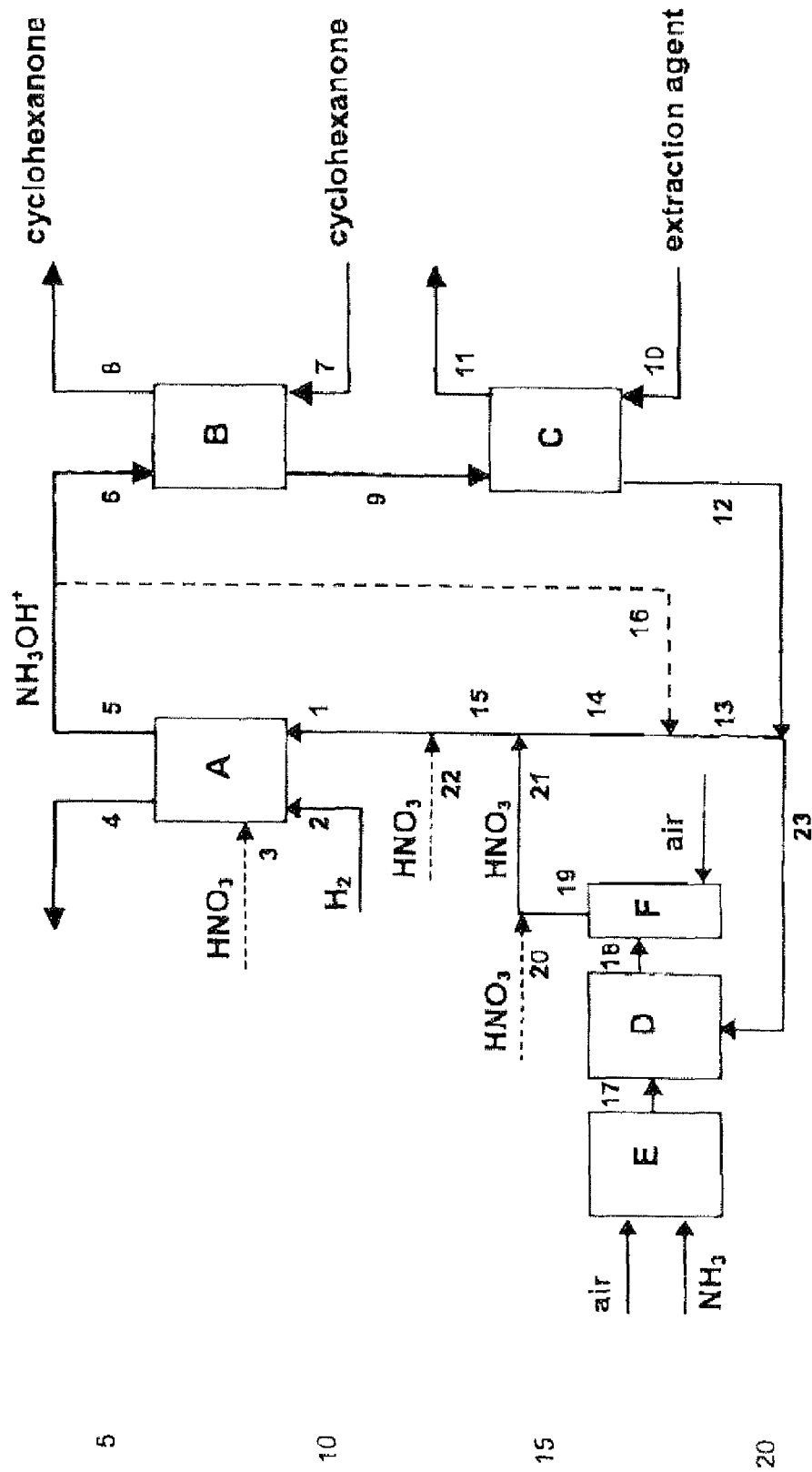
FIG. 1 is a schematic diagram of an embodiment of the process according to the present invention.

Referring to FIG. 1, A represents the hydroxylammonium reactor. B represents the cyclohexanone oxime reactor. To reactor A, containing catalyst, an acidic aqueous solution comprising hydroxylammonium, phosphate and nitric acid is fed as aqueous reaction medium through line 1 and hydrogen is fed through line 2; optionally an additional acidic aqueous solution comprising nitric acid is fed to reactor A through line 3; unreacted hydrogen is discharged, with any other gases, via line 4. In the hydroxylammonium reactor A, the aqueous reaction medium is enriched in hydroxylammonium. This aqueous reaction medium being enriched in hydroxylammonium leaves reactor A via line 5 and is cycled to the cyclohexanone oxime reactor B via line 6. The cyclohexanone to be converted is fed to reactor B via line 7. The largest part of cyclohexanone oxime produced and dissolved in an organic solvent is removed from the system via line 8. The aqueous reaction medium leaving the cyclohexanone oxime reactor through line 9 is extracted in an extraction zone C. An extraction agent, an organic solvent, enters extraction zone C through line 10. Within extraction zone C, additional cyclohexanone oxime is removed from the aqueous reaction medium and carried out of zone C in the organic solvent and is fed through line 11 to zone B.

The aqueous reaction medium leaving extraction zone C through line 12 is recycled to the hydroxylammonium reactor A, through lines 13, 14, 13, and 1. A part of the aqueous reaction medium leaving the extraction zone C through line 12 is tapped for absorbing and oxidizing nitrogen oxides. This part of the aqueous reaction medium is fed through line 23 to absorption column D, in which nitrogen oxides are absorbed, which are produced in reactor E by ammonia combustion and fed through line 18 to absorption column D. In column D nitric acid is produced from absorbed nitrogen oxides by a further reaction with water from the aqueous reaction medium. The aqueous reaction medium enriched with nitric acid passes from column D to bleaching column F through line 18. In column F residual nitrogen oxides are oxidized into nitric acid. Accordingly, the nitric acid concentration is increased in the aqueous reaction medium leaving column F through line 19. Optionally an additional amount of nitric acid can be supplied through line 20 and mixed with the acidic aqueous solution comprising nitric acid passing through line 19. The thus obtained second acidic aqueous solution comprising nitric acid passing through line 21 is mixed with the aqueous reaction medium passing through line 14, the first acidic aqueous solution. Optionally an additional amount of nitric acid can be supplied through line 22 and mixed with the third acidic aqueous solution passing through line 15.

Subsequently the thus obtained third or fourth acidic aqueous solution is fed to the hydroxylammonium reactor through line 1, completing the cycle. The aqueous reaction medium passing through line 13 may be enriched with hydroxylammonium by adding an aqueous solution comprising hydroxylammonium through line 16, which may be tapped from line 5.

Preferably, this process is carried out continuously.

The invention will be elucidated by the following examples, however these are not intended to limit the scope of the invention in any way.

EXAMPLES

In all examples the hydroxylammonium concentration in the acidic aqueous solution was determined by a potentiometric titration with $K_3Fe(CN)_6$.

In all examples the total acid concentration in the acidic aqueous solution was determined by titration up to the first equivalence point of $H_3PO_4$ (approx. pH 4.2) with NaOH.

In all examples the phosphate concentration in the acidic aqueous solution was determined by titration with $La(NO_3)_3$.

In all examples decomposition of hydroxylammonium was monitored by monitoring gas evolution in the third acidic aqueous solution with a bubbler.

Comparative Experiment A

A glass reactor equipped with baffles and a turbine stirrer was filled with 40 ml of a first acidic aqueous solution, comprising per liter 0.029 mole hydroxylammonium, 4.51 mole phosphate, 3.52 mol ammonium and 1.51 mole nitrate, the total acid concentration being 2.67 mole per liter. This first acidic aqueous solution was heated to 65° C. under a continuous stream of nitrogen gas and vigorous stirring (600 rpm). After the solution has reached the desired temperature the supply of nitrogen was stopped and 30 ml of a second acidic aqueous solution, comprising per liter no hydroxylammonium, and 2.83 mole phosphate, 1.53 mole ammonium and 6.44 mole nitrate, having a total acid concentration of 7.53 mole per liter, was mixed with the first acidic aqueous solution drop wise. At a certain point during the addition of the second acidic aqueous solution decomposition of hydroxylammonium starts, which was observed by a vigorous gas evolution. After the addition of the second acidic aqueous solution was completed and the gas evolution in the third acidic aqueous solution having a temperature of 65° C. had stopped the hydroxylammonium concentration in the third acidic aqueous solution was determined by titration and appeared to be <0.001 mol/l whereas the calculated final hydroxylammonium concentration is 0.017 mol/l. In this example decomposition of hydroxylammonium occurred. In the third acidic aqueous solution of this comparative Experiment the calculated total acid concentration is 4.75 mol/l and the calculated phosphate concentration is 3.79 mol/l. Thus in the third acidic aqueous solution the total acid concentration minus the phosphate concentration is 0.96 mol/l. The calculated value for $0.523*\ln([hydroxylammonium]/1.25)+422/(T+81)$ is 0.63. Thus this comparative Experiment demonstrates decomposition of hydroxylammonium in the case that the total acid concentration minus the phosphate concentration in the third acidic aqueous solution is higher than $0.523*\ln([hydroxylammonium]/1.25)+422/(T+81)$.

Example I

Comparative Experiment A was repeated except that instead of 30 ml, 20 ml of the second acidic aqueous solution was mixed with the first acidic aqueous solution. In this case no vigorous gas evolution could be observed. In the third acidic aqueous solution having a temperature of 65° C. the hydroxylammonium concentration determined by titration was 0.018 mol/l, which is equal to the calculated value of 0.019. The calculated total acid concentration minus the calculated phosphate concentration in the third acidic aqueous solution of this Example is 0.3 mol/l. The calculated value for $0.523*\ln([hydroxylammonium]/1.25)+422/(T+81)$ is 0.7. Thus this example demonstrates that no decomposition of hydroxylammonium occurs in the third acidic aqueous solution when the total acid concentration minus the phosphate concentration in the third acidic aqueous solution is lower than $0.523*\ln([hydroxylammonium]/1.25)+422/(T+81)$.

Example II

Comparative Experiment A was repeated except that the third acidic aqueous solution was heated to 35° C. No vigorous gas evolution could be observed. In the third acidic aqueous solution the hydroxylammonium concentration determined by titration was 0.017 mol/l, which is equal to the calculated hydroxylammonium concentration, being 0.017 mol/l. The calculated total acid concentration minus the calculated phosphate concentration in the third acidic aqueous solution of this Example is 1.2 mol/l. The calculated value for $0.523*\ln([hydroxylammonium]/1.25)+422/(T+81)$ is 1.4. Thus this Example demonstrates that no decomposition of hydroxylammonium occurs in the third acidic aqueous solution at a temperature of 35° C. when the total acid concentration minus the phosphate concentration in the third acidic aqueous solution is lower than $0.523*\ln([hydroxylammonium]/1.25)+422/(T+81)$.

Example III

Comparative Experiment A was repeated except that as first acidic aqueous solution, was used a solution comprising per liter 0.146 mole hydroxylammonium, 3.74 mole phosphate, 3.34 mole ammonium and 2.57 mol nitrate, the total acid concentration being 2.33 mol per liter. No vigorous gas evolution could be observed. In the third acidic aqueous solution having a temperature of 65° C. the hydroxylammonium concentration determined by titration was 0.08 mol/l, which is equal to the calculated hydroxylammonium concentration, being 0.08 mol/l. The calculated total acid concentration minus the calculated phosphate concentration in the third acidic aqueous solution of this Example is 1.2 mol/l. The calculated value for $0.523*\ln([\text{hydroxylammonium}]1.25)+422/(T+81)$ is 1.5. Thus this Example demonstrates that no decomposition of hydroxylammonium occurs in the third acidic aqueous solution when the total acid concentration minus the phosphate concentration in the third acidic aqueous solution is lower than $0.523*\ln([\text{hydroxylammonium}]/1.25)+422/(T+81)$.

Examples IV-XXIV

Comparative Experiment A was repeated except that different first and second acidic aqueous solutions and temperatures were used and that the addition of the second acidic aqueous solution was stopped at the moment gas evolution started. At that moment the amount of added second acidic aqueous solutions was determined, the total acid concentration minus the phosphate concentration in the third acidic aqueous solution was calculated, the value for $0.523*\ln([\text{hydroxylammonium}]/1.25)+422/(T+81)$ in the third acidic aqueous solution was calculated and the amount of hydroxylammonium was calculated. All data are given in Tables 1-3. These Examples show that decomposition of hydroxylammonium starts at the point where the total acid concentration minus the phosphate concentration in the third acidic aqueous solution is equal to $0.523*\ln([\text{hydroxylammonium}]/1.25)+422/(T+81)$.

TABLE 1

| First acidic aqueous solution | Amount of hydroxyl- ammonium in mol/l | Total acid concen- tration in mol/l | Phosphate concen- tration in mol/l | Ammonium concen- tration in mol/l | Nitrate concen- tration in mol/l |
|---|---|---|---|---|---|
| A1 | 0.090 | 2.39 | 3.80 | 4.80 | 3.02 |
| A2 | 0.029 | 2.67 | 4.51 | 3.52 | 1.51 |
| A3 | 0.146 | 2.33 | 3.74 | 3.34 | 2.57 |
| A4 | 0.020 | 2.74 | 4.55 | 3.32 | 1.42 |

TABLE 2

Second acidic aqueous solution

| Second acidic aqueous solution | Amount of hydroxylammonium in mol/l | Total acid concentration in mol/l | Phosphate concentration in mol/l | Ammonium concentration in mol/l | Nitrate concentration in mol/l |
|---|---|---|---|---|---|
| B1 | 0 | 5.79 | 2.50 | 2.30 | 5.75 |
| B2 | 0 | 7.53 | 2.83 | 1.53 | 6.44 |
| B3 | 0 | 8.81 | 1.90 | 0.47 | 7.31 |
| B4 | 0 | 7.70 | 2.90 | 1.20 | 6.11 |

TABLE 3

Comparison of the amount of [total acid] − [phosphate] with $0.523*\ln([\text{hydroxylammonium}]/1.25) + 422/(T + 81)$

| Example | First acidic aqueous solution | Amount of first Acidic aqueous solution in ml | Second acidic aqueous solution | Amount of second Acidic aqueous solution in ml | T in °C. | [hydroxyl- ammonium] in third acidic aqueous solution | Amount of [total acid] − [phosphate] in third acidic aq. solution | $0.523*\ln([\text{hydroxyl-ammonium}]/1.25) + 422/(T + 81)$ |
|---|---|---|---|---|---|---|---|---|
| IV | A1 | 40.0 | B1 | 90.2 | 25 | 0.028 | 1.9 | 2.0 |
| V | A1 | 40.0 | B1 | 75.5 | 35 | 0.031 | 1.7 | 1.7 |
| VI | A1 | 40.0 | B1 | 66.5 | 45 | 0.034 | 1.5 | 1.5 |
| VII | A1 | 40.0 | B1 | 60.0 | 55 | 0.036 | 1.4 | 1.3 |
| VIII | A1 | 40.0 | B3 | 33.6 | 25 | 0.049 | 2.4 | 2.3 |
| IX | A1 | 40.0 | B3 | 29.0 | 35 | 0.052 | 2.1 | 2.0 |
| X | A1 | 40.0 | B3 | 24.5 | 45 | 0.056 | 1.8 | 1.7 |
| XI | A1 | 40.0 | B3 | 22.5 | 55 | 0.057 | 1.6 | 1.5 |
| XII | A2 | 40.0 | B2 | 33.0 | 45 | 0.016 | 1.1 | 1.0 |
| XIII | A2 | 40.0 | B2 | 29.8 | 55 | 0.016 | 1.0 | 0.8 |
| XIV | A2 | 40.0 | B2 | 25.5 | 65 | 0.017 | 0.7 | 0.7 |
| XV | A2 | 40.0 | B2 | 22.2 | 75 | 0.018 | 0.5 | 0.5 |
| XVI | A3 | 40.0 | B3 | 42.0 | 25 | 0.071 | 2.9 | 2.5 |
| XVII | A3 | 40.0 | B3 | 36.8 | 35 | 0.076 | 2.6 | 2.2 |
| XVIII | A3 | 40.0 | B3 | 29.4 | 45 | 0.084 | 2.1 | 1.9 |
| XIX | A3 | 40.0 | B3 | 27.4 | 55 | 0.086 | 2.0 | 1.7 |
| XX | A4 | 40.0 | B4 | 39.4 | 25 | 0.010 | 1.5 | 1.5 |
| XXI | A4 | 40.0 | B4 | 29.2 | 45 | 0.011 | 1.0 | 0.9 |
| XXII | A4 | 40.0 | B4 | 25.0 | 55 | 0.012 | 0.7 | 0.7 |
| XXIII | A4 | 40.0 | B4 | 21.5 | 65 | 0.013 | 0.5 | 0.5 |
| XXIV | A4 | 40.0 | B4 | 19.2 | 75 | 0.013 | 0.3 | 0.3 |

Example XXV

Comparative Experiment A was repeated except that glass reactor equipped with baffles and a turbine stirrer was filled with 75 ml of a first acidic aqueous solution, comprising per liter 1.58 mole hydroxylammonium, 3.76 mole phosphate, 3.94 mole ammonium, and 1.37 mole nitrate, the total acid concentration being 0.74 mole/l. Under vigorous stirring (600 rpm) at a temperature of 60° C. 120 ml of a mixture of 6 parts of an acidic aqueous solution, comprising per liter no hydroxylammonium, 2.90 mole phosphate 1,20 mole ammonium, and 6.11 mole nitrate, the total acid concentration being 7.70 mole per liter and one part of a 65% aqueous nitric acid solution were mixed with the first acidic aqueous solution. At the moment gas evolution started the calculated hydroxylammonium concentration in the third acidic aqueous solution having a temperature of 60° C. was 0.61 mol/l. The calculated total acid concentration minus the calculated phosphate concentration in the third acidic aqueous solution of this Example is 2.7 mol/l. The calculated value for $0.523*\ln([\text{hydroxylammonium}]/1.25)+422/(T+81)$ is 2.6. This Experiment demonstrates that in the third acidic aqueous solution comprising per liter 0.61 mole hydroxylammonium, obtained by mixing a first acidic aqueous solution with a second acidic aqueous solution which is obtained by mixing an acidic aqueous solution comprising nitric acid and phosphate with a 65% nitric acid solution, decomposition of hydroxylammonium starts at the moment that the total acid concentration minus the phosphate concentration in the third acidic aqueous solution is equal to $0.523*\ln([\text{hydroxylammonium}]/1.25)+422/(T+81)$.

Example XXVI

Example XXV was repeated except that for the second acidic aqueous solution a 65% aqueous nitric acid solution is used which was added drop wise to the first acidic aqueous solution until gas evolution started. At the moment gas evolution started 41 ml of the 65% aqueous nitric acid solution has been added and the calculated hydroxylammonium concentration in the third acidic aqueous solution having a temperature of 60° C. was 1.02 mol/l. The calculated total acid concentration minus the calculated phosphate concentration in the third acidic aqueous solution of this Example is 3.2 mol/l. The calculated value for $0.523*\ln([\text{hydroxylammonium}]/1.25)+422/(T+81)$ is 2.9. This Example demonstrates that if the concentration of hydroxylammonium in the third acidic aqueous solution is 1.02 mol/l and the second acidic aqueous solution, being a 65% aqueous nitric acid solution, is mixed drop wise with the first acidic aqueous solution no decomposition occurs until the total acid concentration minus the phosphate concentration in the third acidic aqueous solution is equal to $0.523*\ln([\text{hydroxylammonium}]/1.25)+422/(T+81)$.

Comparative Experiment B

Comparative Experiment A was repeated except that the glass reactor equipped with baffles and a turbine stirrer was filled with 70 ml of a first acidic aqueous solution, comprising per liter 0.020 mole hydroxylammonium, 4.55 mole phosphate, 3.32 mol ammonium, and 1.42 mole nitrate, the total acid concentration being 2.74 mole/l. Under vigorous stirring (600 rpm) at a temperature of 45° C. 30 ml of a second acidic aqueous solution, comprising per liter no hydroxylammonium, 7.70 mole total acid and 2.90 mole phosphate and 6 ml of a 65% aqueous nitric acid solution were mixed with the first acidic aqueous solution. Gas evolution was observed. After the gas evolution had stopped the hydroxylammonium concentration in the third acidic aqueous solution was determined by titration and appeared to be <0.001 mol/l. The calculated hydroxylammonium concentration in the third acidic aqueous solution having a temperature of 45° C. was 0.013 mol/l. The calculated total acid concentration minus the calculated phosphate concentration in the third acidic aqueous solution of this comparative Experiment is 1.0 mol/l and the calculated value for $0.523*\ln([\text{hydroxylammonium}]/1.25)+422/(T+81)$ is 0.96. This comparative Experiment demonstrates that in the third acidic aqueous solution having a temperature of 45° C. and a hydroxylammonium concentration of 0.013 mol/l, obtained by mixing a first acidic aqueous solution with a second acidic aqueous solution which is obtained by mixing an acidic aqueous solution comprising nitric acid and phosphate with a 65% nitric acid solution, decomposition of hydroxylammonium occurs when the total acid concentration minus the phosphate concentration in the third acidic aqueous solution is equal to $0.523*\ln([\text{hydroxylammonium}]/1.25)+422/(T+81)$.

Example XXVII

Comparative Experiment B was repeated except that the hydroxylammonium concentration in the first acidic aqueous solution has been increased by adding 5 ml of an aqueous hydroxylammonium solution, comprising per liter 1.58 mole hydroxylammonium, 3.76 mole phosphate, 3.94 mole ammonium and 1.37 mole nitrate having a total acid concentration of 0.74 mole/l to 70 ml of a first acidic aqueous solution comprising per liter 0.020 mole hydroxylammonium, 4.55 mole phosphate, 3.32 mole ammonium and 1.42 mole nitrate having a total acid concentration of 2.74 mole per liter. No gas evolution was observed. The calculated hydroxylammonium concentration in the third acidic aqueous solution having a temperature of 45° C. was 0.084 mol/l. The calculated total acid concentration minus the calculated phosphate concentration in the third acidic aqueous solution of this Example is 0.8 mol/l and the calculated value for $0.523*\ln([\text{hydroxylammonium}]/1.25)+422/(T+81)$ is 1.9. This Example demonstrates that increasing the amount of hydroxylammonium in the third acidic aqueous solution in such a way that the total acid concentration minus the phosphate concentration in the third acidic aqueous solution is lower than $0.523*\ln([\text{hydroxylammonium}]/1.25)+422/(T+81)$, results in preventing decomposition of hydroxylammonium in the third acidic aqueous solution.

The invention claimed is:

1. Process for producing cyclohexanone oxime comprising:
    cycling an aqueous reaction medium containing residual hydroxylammonium from a cyclohexanone oxime synthesis reactor in which cyclohexanone oxime is produced by reaction of hydroxylammonium with cyclohexanone to a hydroxylammonium synthesis reactor in which hydroxylammonium is prepared by catalytic reduction of nitrate with hydrogen;
    providing a first acidic aqueous solution comprising hydroxylammonium and phosphate from at least a portion of the cycled aqueous reaction medium; and
    mixing the first acidic aqueous solution with a second acidic aqueous solution comprising nitric acid within or upstream of the hydroxylammonium synthesis reactor, resulting in a third acidic aqueous solution comprising hydroxylammonium, phosphate and nitric acid, wherein
    the third acidic aqueous solution has a total acid concentration minus the phosphate concentration which is lower than $0.523*\ln([\text{hydroxylammonium}]/1.25)+422/$ (T+8l) whereby [hydroxylammonium] is the concentration of hydroxylammonium in the third acidic aqueous solution, T is the temperature of the third acidic aqueous solution expressed in °C. and all concentrations are expressed in mol/l.

2. Process according to claim 1, wherein $$(c_{acid}(1)*V_1+c_{acid}(2)*V_2)/(V_1+V_2)-(c_{phosphate}(1)*V_1+c_{phosphate}(2)*V_2)/(V_1+V_2)<0.523*\ln(((c_{hyam}(1)*V_1+c_{hyam}(2)*V_2/V_1V_2))/1.25)+422/(T(3)+81)$$

wherein
- $c_{acid}(1)$ and $c_{acid}(2)$ are the total acid concentration in the first acidic aqueous solution and in the second acidic aqueous solution respectively, expressed in mol/l,
- $c_{phosphate}(1)$ and $c_{phosphate}(2)$ are the phosphate concentration in the first acidic aqueous solution and in the second acidic aqueous solution respectively, expressed in mol/l,
- $c_{hyam}(1)$ and $c_{haym}(2)$ are concentration hydroxylammonium in the first acidic aqueous solution and in the second acidic aqueous solution respectively, expressed in mol/l,
- T(3) is the temperature of the third acidic aqueous solution,
- $V_1$ and $V_2$ are the volume of the first acidic aqueous solution and second acidic aqueous solution respectively.

3. Process according to claim 1, wherein providing the first acidic aqueous solution comprises adding hydroxylammonium to the first acidic aqueous solution upstream of the hydroxylammonium synthesis reactor.

4. Process according to claim 3, wherein the aqueous reaction medium discharged from the cyclohexanone oxime synthesis reactor is separated into at least a first part and a second part; and wherein the process comprises adding said hydroxylammonium to the first part of the aqueous reaction medium upstream of the hydroxylammonium synthesis reactor to obtain the first acidic aqueous solution; and wherein the second part is directed to an absorber unit for absorbing and/or oxidizing nitrogen oxides in the second part of the aqueous reaction medium to prepare nitric acid therefrom.

5. Process according to claim 1, wherein the process comprises adding hydroxylammonium to the third acidic aqueous solution.

6. Process according claim 1, further comprising separating a portion of a hydroxylammonium enriched aqueous reaction medium discharged from the hydroxylammonium synthesis reactor and adding the separated portion of the hydroxylammonium enriched aqueous reaction medium to the aqueous reaction medium.

7. Process according to claim 1, wherein the process comprises feeding the third acidic aqueous solution to the hydroxylammonium synthesis reactor.

8. Process according to claim 1, comprising mixing the third acidic aqueous solution with an acidic aqueous solution comprising nitric acid at a temperature between 20 and 80° C., resulting in a fourth acidic aqueous solution comprising hydroxylammonium, phosphate and nitric acid wherein $$c_{acid}(4)-c_{phosphate}(4)<0.523*\ln(c_{hyam}(4)/1.25)+422/(T(4)+81)$$

wherein
- $c_{acid}(4)$=total acid concentration in the fourth acidic aqueous solution, expressed in mol/l,
- $c_{phosphate}(4)$=phosphate concentration in the fourth acidic aqueous solution, expressed in mol/l,
- $c_{hyam}(4)$=concentration hydroxylammonium in the fourth acidic aqueous solution, expressed in mol/l,
- T(4)=temperature in the fourth acidic aqueous solution expressed in °C.

9. Process according to claim 8, wherein the process comprises feeding the fourth acidic aqueous solution to the hydroxylammonium synthesis reactor.

10. Process according to claim 8, wherein the process comprises adding hydroxylammonium to the third acidic aqueous solution.

11. Process according to claim 10, further comprising separating a portion of a hydroxylammonium enriched aqueous reaction medium discharged from the hydroxylammonium synthesis reactor and add adding the separated portion of the hydroxylammonium enriched aqueous reaction medium to the third acidic aqueous solution.

12. Process according to claim 1, wherein the mixing of the first acidic aqueous solution and second acidic aqueous solution is performed in the hydroxylammonium synthesis reactor.

13. Process according to claim 8, wherein the mixing of the third acidic aqueous solution and said acidic aqueous solution comprising nitric acid is performed in the hydroxylammonium synthesis reactor.

14. Process according to claim 1, wherein the first acidic aqueous solution is an aqueous reaction medium discharged from the cyclohexanone oxime synthesis reactor.

15. Process according to claim 1, wherein the second acidic aqueous solution is obtained by absorbing and oxidizing nitrogen oxides in an aqueous solution.

16. Process according to claim 1, wherein said mixing of the first acidic aqueous solution with the second acidic aqueous solution is carried out at a temperature between 20 and 80° C.

17. Process according to claim 1, wherein the second acidic aqueous solution comprises nitric oxide.

18. Process according to claim 17, comprising separately feeding the first and second acidic aqueous solutions to the hydroxylammonium synthesis reactor, and mixing the first and second acidic aqueous solutions within the hydroxylammonium synthesis reactor so that the third acidic aqueous solution is present in the hydroxylammonium synthesis reactor.

* * * * *